(12) United States Patent
Jeffrey

(10) Patent No.: US 8,267,916 B2
(45) Date of Patent: Sep. 18, 2012

(54) GUIDEWIRE REPLACEMENT DEVICE

(75) Inventor: Andrew Jeffrey, Tübingen (DE)

(73) Assignee: Abbott Laboratories, Abbott Park, IL (US)

( * ) Notice: Subject to any disclaimer, the term of this patent is extended or adjusted under 35 U.S.C. 154(b) by 394 days.

(21) Appl. No.: 12/563,864

(22) Filed: Sep. 21, 2009

(65) Prior Publication Data

US 2010/0082014 A1    Apr. 1, 2010

Related U.S. Application Data

(60) Provisional application No. 61/101,569, filed on Sep. 30, 2008.

(51) Int. Cl.
*A61M 25/00* (2006.01)

(52) U.S. Cl. .................... 604/528; 604/103.04; 600/585

(58) Field of Classification Search ............. 604/103.04, 604/164.13, 528; 600/585
See application file for complete search history.

(56) References Cited

U.S. PATENT DOCUMENTS

2006/0142703 A1 *  6/2006  Carter et al. .................. 604/264

OTHER PUBLICATIONS

U.S. Appl. No. 61/101,569, filed Sep. 30, 2008, Jeffrey.

* cited by examiner

*Primary Examiner* — Bhisma Mehta
(74) *Attorney, Agent, or Firm* — Workman Nydegger

(57) ABSTRACT

A guidewire exchange device is configured to exchange a guidewire associated with a guidewire port in a medical device. The guidewire exchange device is further configured to interface with the medical device at the guidewire port, remove the guidewire from the medical device, and insert a replacement guidewire.

16 Claims, 8 Drawing Sheets

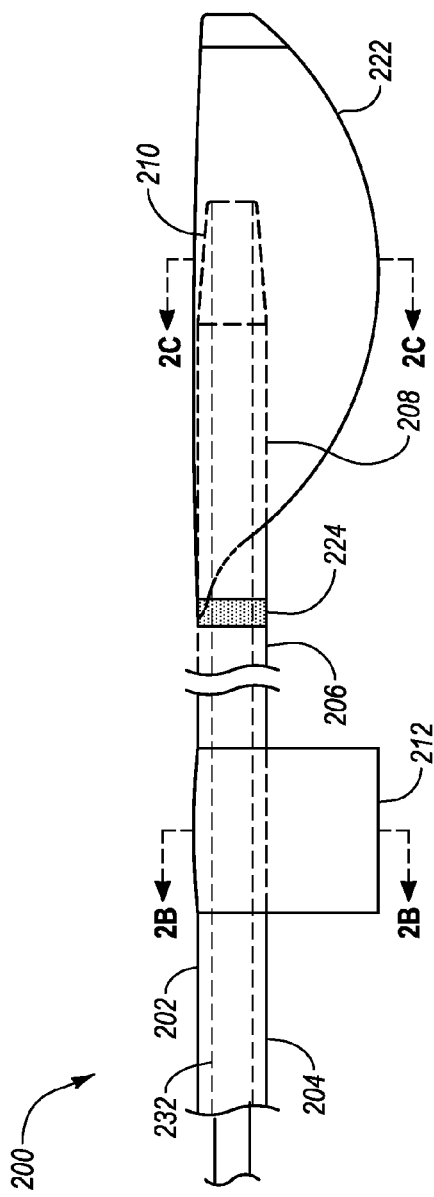
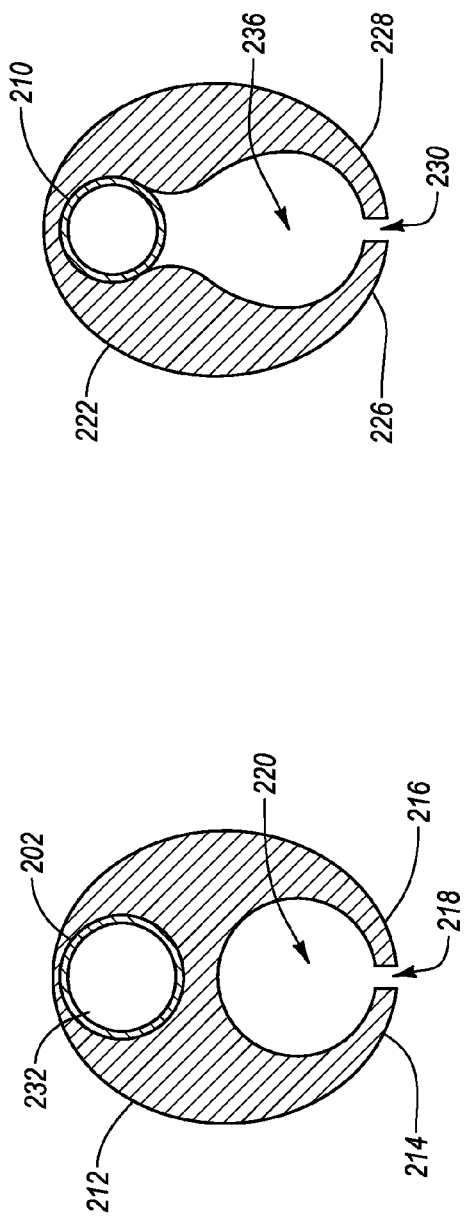

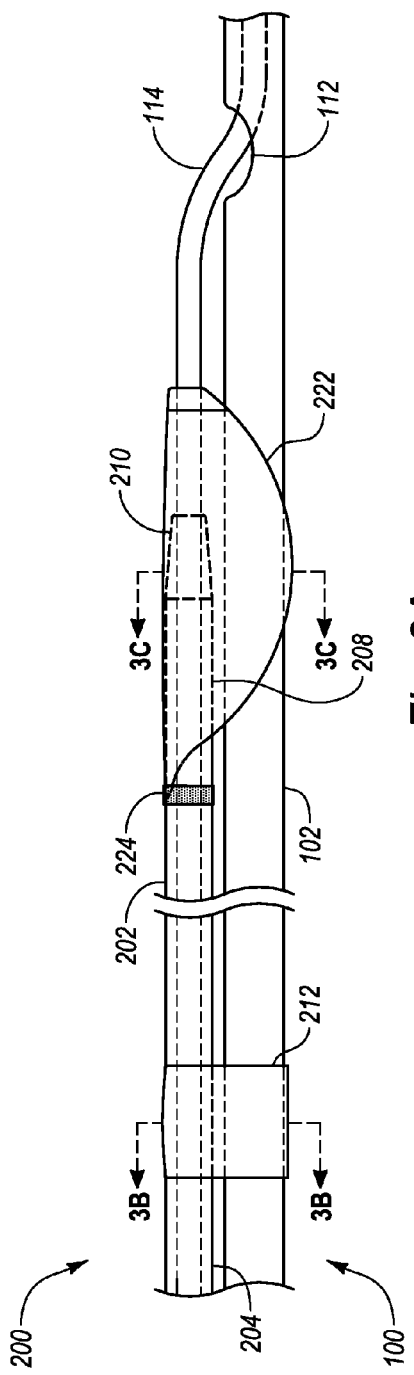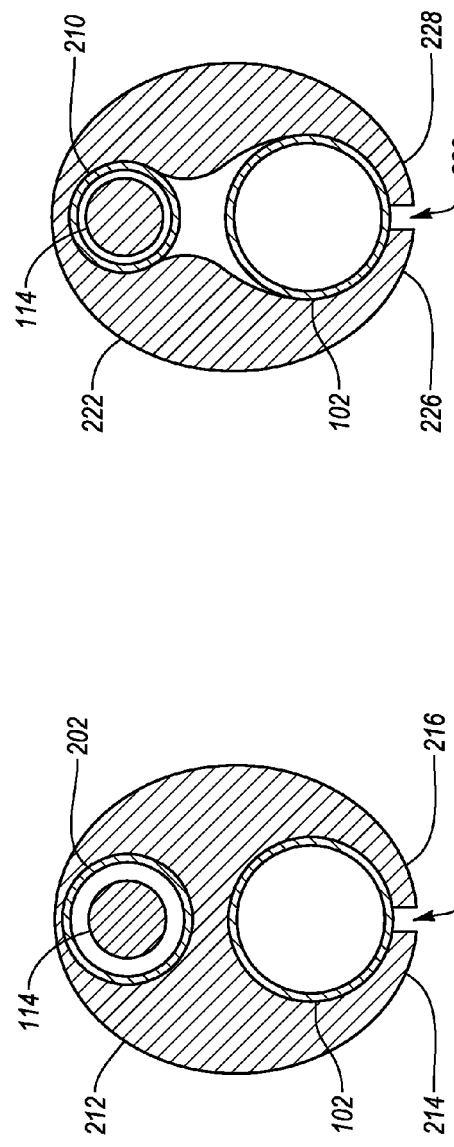

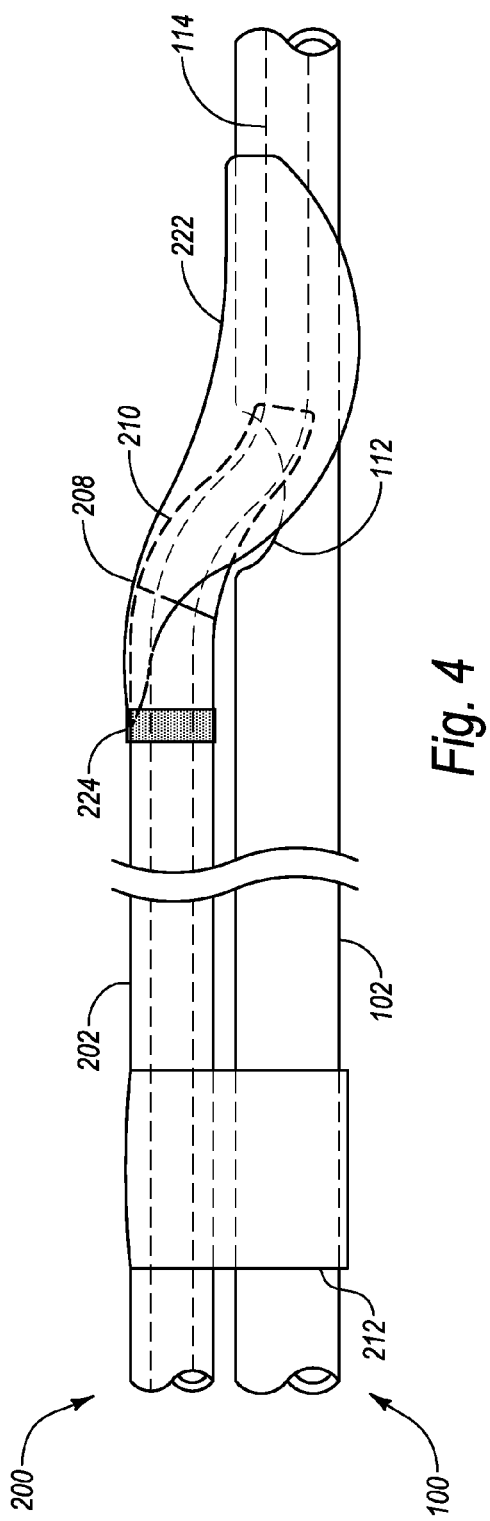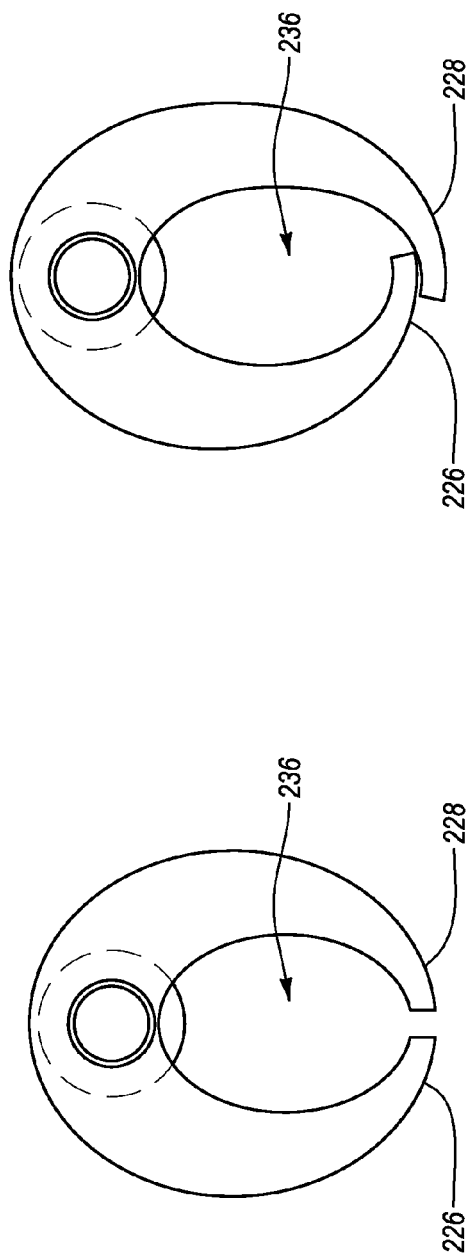

GUIDEWIRE REPLACEMENT DEVICE

CROSS REFERENCE

This application claims the benefit of, and priority to, U.S. Provisional Patent Application Ser. No. 61/101,569, filed on Sep. 30, 2008 and entitled "RAPID-EXCHANGE GUIDEWIRE REPLACEMENT DEVICE," which is incorporated in its entirety herein by this reference.

BACKGROUND OF THE INVENTION

1. The Field of the Invention

The present invention relates generally to medical devices and more particularly the present invention relates to devices and methods for facilitating guidewire exchange for medical devices with a rapid exchange port.

2. The Relevant Technology

Medical devices such as catheters are generally designed to be guided to a desired location over a rail such as a guidewire. The medical device may be constructed so that the entire length of the medical device is guided over the guidewire. Medical devices having this type of embodiment are generally referred to as over the wire "OTW" medical devices.

Another type of medical device is known as a rapid-exchange "RX" device. In this embodiment only a portion of the medical device is passed over the guidewire to direct the medical device to a desired location. Generally the guidewire would enter a lumen at the distal end of the device and exit the lumen through an RX port located a relatively short distance from the distal end of the device. The benefits of a RX medical device are its ability to be more easily inserted into a patient or located to a particular location. Additionally, a shorter guidewire may be utilized, as the entire length of the medical device does not have to be passed over the guidewire.

With an OTW medical device, the user can hold the medical device in position, remove the guidewire from the lumen of the medical device and then insert a new guidewire in place of the old guidewire. In this case, the lumen of the medical device will guide the guidewire to the location of the previous guidewire.

However, one drawback to RX designs versus OTW designs is that the guidewire cannot be easily removed and replaced in the medical device once the medical device has been inserted into a patient. This is so because the entire length of the RX medical device does not capture the guidewire like the OTW device.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods and devices for guidewire exchange for medical devices. Embodiments of the invention can be configured to place an uncoupled segmented vascular endoprosthesis within a body lumen.

In one example embodiment, a guidewire exchange device is configured to exchange a guidewire associated with a guidewire port on a medical device. The guidewire exchange device is further configured to interface with the medical device at the guidewire port, remove the guidewire from the medical device, and insert a replacement guidewire. The guidewire exchange device may include an elongate body that has a proximal end and a distal end, and a passage that extends from the proximal end towards the distal end. A tip portion may also be included as part of the guidewire exchange device, the tip portion attached adjacent to the distal end of the elongate body with an aperture located on a distal end of the tip portion. The aperture may be configured to cooperate with the passage within the elongate body. Furthermore, the tip portion may be configured to interface with the guidewire port on the medical device.

In another example embodiment, a guidewire exchange system for exchanging a guidewire is disclosed. The guidewire exchange system may include a first and second guidewire and a medical device having a first configuration where the medical device is associated with the first guidewire. The medical device may also include a second configuration where the medical device is associated with a second guidewire. The guidewire exchange system may also include a guidewire exchange device that interfaces with the medical device to change the medical device from the first configuration to the second configuration.

Additionally, a further embodiment includes a method for exchanging a guidewire in a medical device. The method may include the act of disposing a guidewire exchange device over a guidewire, the guidewire exchange device including a tip portion. The method may further include the act of engaging a portion of the tip portion with a guidewire port associated with a medical device. Moreover, the method may include removing the guidewire from the medical device and inserting a second guidewire in the medical device through the tip portion.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify at least some of advantages and features of the present invention, a more particular description of the invention will be rendered by reference to specific embodiments thereof which are illustrated in the appended drawings. It is appreciated that these drawings depict only illustrated embodiments of the invention and are, therefore, not to be considered limiting of its scope. It should be noted that the figures are not drawn to scale and that elements of similar structures or functions are generally represented by like reference numerals for illustrative purposes throughout the figures. It also should be noted that the figures are only intended to facilitate the description of example embodiments of the present invention. The invention will be described and explained with additional specificity and detail through the use of the accompanying drawings in which:

FIG. 2A is an illustration of an example embodiment of a guidewire exchange device in accordance with the present invention;

FIGS. 2B and 2C are cross-sectional views of an example guidewire exchange device in accordance with the present invention;

FIG. 3A is an illustration of an example guidewire exchange device engaged with an example medical device;

FIGS. 3B and 3C are cross-sectional views of an example guidewire exchange device engaged with an example medical device in accordance with the present invention;

FIG. 4 is a close-up view of an example guidewire exchange device interfaced with an example medical device;

FIGS. 5A and 5B illustrate example cross-sectional views of an example grip extension of an example guidewire exchange device;

DETAILED DESCRIPTION

In general, the present invention relates to devices, systems, and methods for exchanging a guidewire associated with a medical device while the medical device is in use or otherwise within or associated with the anatomy of a patient. More particularly, the examples of the present invention relate to a guidewire exchange device configured to engage a medical device, which is positioned within the anatomy of a patient, and exchange a first guidewire with a second guidewire.

Figure 1A:
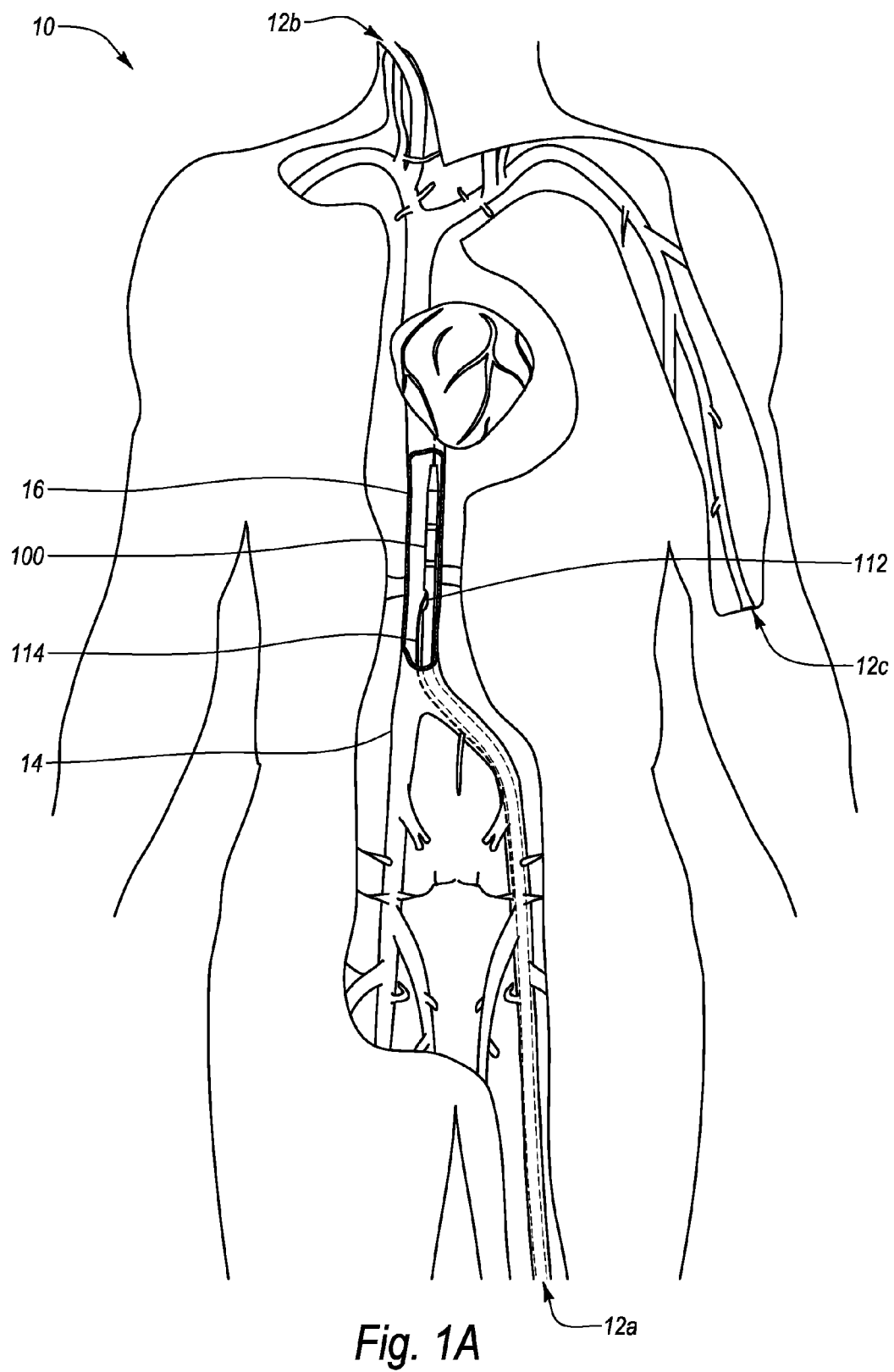
FIGS. 1A and 1B illustrates an exemplary subject for an interluminal medical treatment device.

FIG. 1A illustrates an exemplary subject 10 for a medical device 100. The medical device 100 may be functionally similar to the medical device 100 that will be described in more detail with respect to FIG. 1C. In particular, the medical device 100 may be a rapid exchange type medical device that includes a rapid exchange port (RX port) or guidewire port 112. As illustrated in FIG. 1A, a guidewire 114 may extend through the medical device by way of the RX port 112. The medical device 100 follows the guidewire 114 to a deployment site 16, which is a location within a body lumen 14 of the subject 10. The rapid exchange feature, or the RX port 112, reduces the guidewire friction compared to traditional medical devices that rely on a guidewire for placement, thus the ease at which the medical device 100 with the RX port 112 moves through the body lumen 14 is increased relative to traditional configurations.

Moreover, the RX port 112 allows for a short guidewire to be used. As is illustrated in FIG. 1A, the total length of guidewire required is only the length from a particular deployment site, for example deployment site 16, to the access site, for example 12a. For a medical device without an RX port 112 or similar configuration, the guidewire 114 is typically longer because the guidewire extends throughout the entire medical device 100.

The medical device 100 may be implanted in the body lumen 14 of the subject 10. As illustrated in FIG. 1A, the medical device 100 may be inserted and/or retrieved through an access site 12a, 12b, 12c. In the present embodiment, the access site may include a femoral artery access site 12a, a jugular vein access site 12b, a radial vein access site 12c, femoral vein, brachial vein, brachial artery, other access sites, or combinations thereof.

For instance, the medical device 100 may be inserted through the femoral artery access site 12a and retrieved through the jugular or radial vein access site 12b or 12c. In another example, the medical device 100 may be inserted through the jugular vein access site 12b and retrieved through the femoral artery or radial vein access site 12a or 12c. In a further example, the medical device 100 may be inserted through the radial vein access site 12c and retrieved through the femoral artery or jugular vein access site 12a or 12b. In yet a further example, the medical device 100 may be inserted and retrieved through the radial vein access site 12c. Additionally, the medical device 100 may be inserted and retrieved through the jugular vein access site 12b. Further, the medical device 100 may be inserted and retrieved through the femoral artery access site 12a.

As mentioned above, the medical device 100 may be deployed near a deployment site 16. In one implementation, the deployment site 16 may include a location within a coronary artery. In other implementations, other deployment sites may be used. For example, the deployment site 16 may include central and peripheral arteries and veins, vena cavas, bile ducts, esophagus, colons, trachea, large bronchi, ureters, and urethra.

Figure 1B:
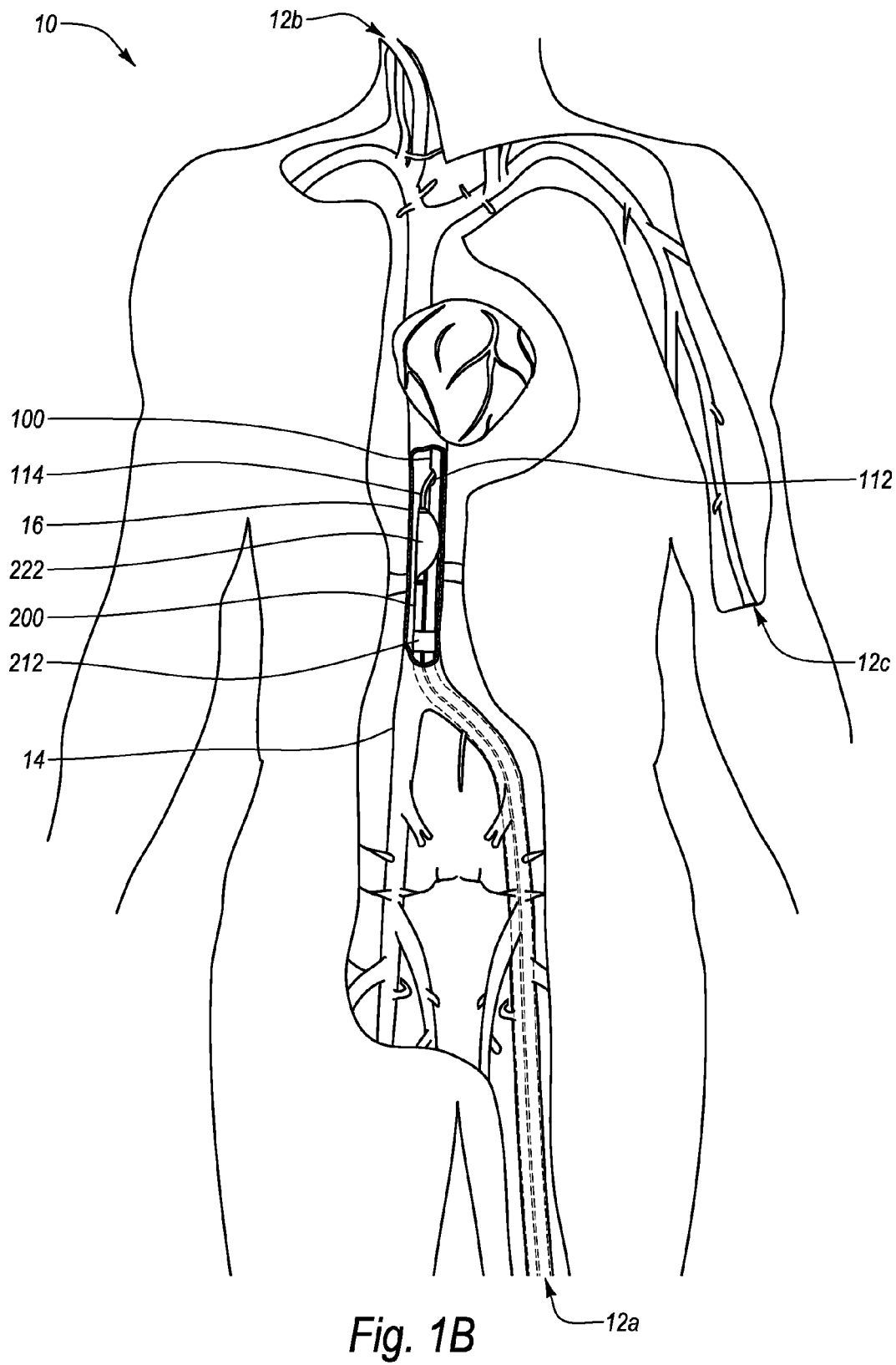

At various points during the use of the medical device 100, and for various reasons, it may become desirable to replace the guidewire 114 associated with the medical device 100. However, it is not desirable to remove the medical device 100 from the patient. Therefore, and as illustrated in FIG. 1B, a guidewire exchange device 200 may be introduced within the body lumen 14 and used to exchange the guidewire 114. In particular, the guidewire exchange device 200 may be passed over the guidewire 114, as illustrated in FIG. 1B, such that the guidewire exchange device 200 ultimately interfaces with the RX port 112 on the medical device 100. Additionally, the guidewire exchange device 100 may include a grip extension 222 and/or a proximal grip 212 that is able to grip on a portion of the medical device 100 as to align the guidewire exchange device 200 with the RX port 112 located on the medical device 100.

In one example, the guidewire exchange device 200 interfaces with the RX port 112 and permits the guidewire 114 to be withdrawn through the guidewire exchange device 200. Next, a second or new guidewire may be inserted through the guidewire exchange device 200 and into the RX port 112 on the medical device 100. Once the new guidewire is properly positioned within the medical device 100, the guidewire exchange device 200 may be removed from the body lumen 14 and from the patient. Additional details and examples of the medical device 100 and the guidewire exchange device 200 are discussed below.

Figure 1C:
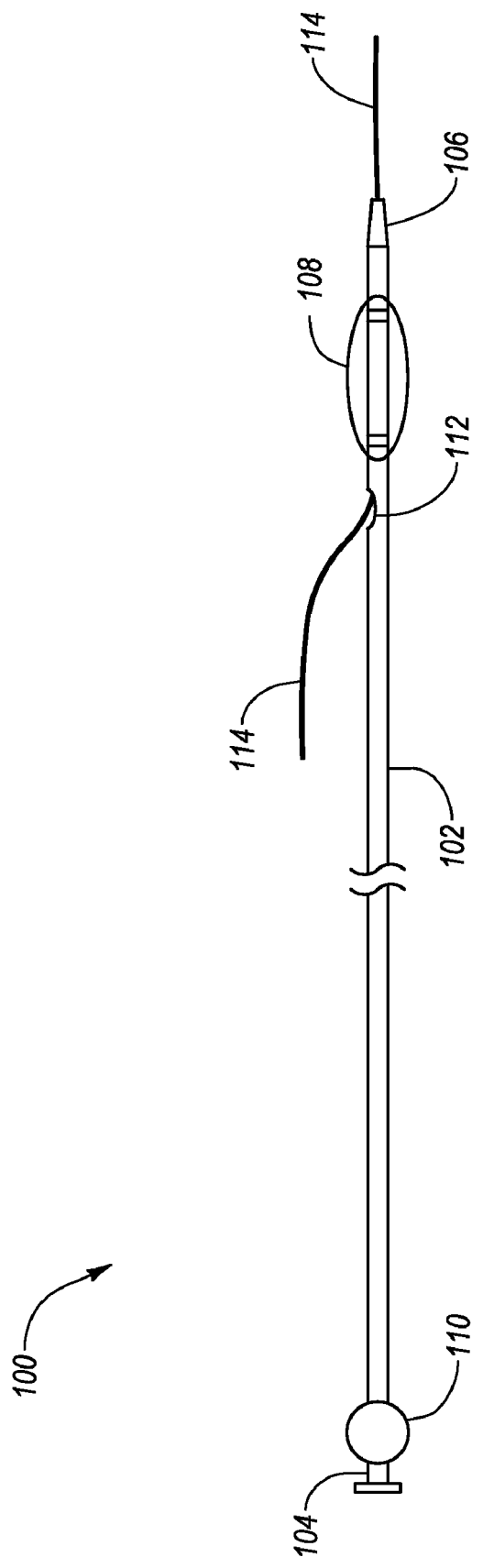
FIG. 1C is an illustration of an example medical device.

FIG. 1C illustrates an example medical device 100. As shown in FIG. 1C, the medical device 100 may be a balloon type or expanding catheter. The medical device 100 may include a shaft 102 that has a proximal end 104 and a distal end 106. The medical device 100 may further include a balloon expansion 108 positioned near the distal end 106 of the shaft 102 and a control 110 located at the proximal end 104 of the medical device 100. As mentioned, the medical device 100, as shown in FIG. 1C, is an RX medical device and has an RX port 112 which is configured such that a guidewire 114 may extend through the RX port 112 and out of the distal end 106 of the medical device 100.

Briefly, in operation, the medical device 100 may be used to introduce various other medical devices, various medicines, or perform various procedures within the anatomy or body lumen, for example, an artery. In order to introduce and position the medical device 100 into the body lumen, the guidewire 114 may be first inserted into the body lumen. The guidewire 114 is then associated with the medical device, i.e., the guidewire 114 is threaded through the medical device 100, such that the medical device 100 may follow the guidewire through the body lumen to the required location within the body lumen.

In one embodiment, for example, FIG. 1C illustrates the medical device as a balloon expansion catheter that may be used to expand a balloon-type stent within an artery or vein or other lumen of a patient's body. The type of medical device, however, may vary from one embodiment to the next. For example, the type of medical device 100 used for the present invention is not restricted to the balloon expansion catheter illustrated in FIG. 1C. Any number of various types of medical devices may be used in accordance with the present invention, for example, delivery sheaths, closure devices, and/or any other intravascular medical devices that are configured or may be configured with an RX port 112 or similar port.

Just as the type of medical device 100 may vary from one embodiment to the next, so too may the configuration of the medical device 100 vary. One way in which the configuration of the medical device 100 may vary is the material of the medical device 100. Generally speaking, the medical device 100 material may be any material or combination of materials. In particular, the medical device 100 may be made from a rigid material such as stainless steel or other biocompatible materials that are rigid. Alternatively, the medical device 100 may be made of a flexible material such as those materials traditionally utilized to make catheter shafts, introducer sheaths or other medical devices. Suitable flexible materials include, but are not limited to, polyvinylchloride (PVC), PEEK, PTFE, Nylon or similar materials.

Not withstanding the material of the medical device 100, the geometric configuration is another way in which the medical device 100 may vary. For example, the RX port 112 is one way in which the geometric configuration of the medical device 100 may vary from one embodiment to the next. As illustrated in FIG. 1C, the RX port 112 may have a substantially circular geometric configuration; however, in other example embodiments the geometric configuration of the RX port may vary. For example, the geometric configuration of the RX port may be, but is not limited to, rectangular, square, triangular, oval or any other configuration or combination of configurations.

Another way in which the RX port 112 may vary is the position of the RX port with respect to the distal end 106 of the medical device 100. For example, and as illustrated in FIG. 1C, the RX port 112 may be positioned just a short distance from the distal end 106 of the medical device 100. Example distances would include a distance of about 50 millimeters from the distal end 106 of the medical device 100. However, the distance between the distal end 106 and the RX port 112 may be larger or smaller depending on the design and configuration of the medical device 100.

Related to the distance from the distal end 106 of the medical device 100 to the RX port 112 is the position of the RX port with respect to any functionality (i.e. the balloon expansion 108). For example, and as shown in FIG. 1C, the RX port 112 is located on the proximal side of the balloon expansion 108. In other embodiments, however, the RX port 112 may be located on the distal side of the balloon expansion 108. The RX port 112 location, with respect to any functionality or functional feature of the medical device 100, may vary depending on the type of function that is performed and the nature and configuration of the specific medical device. For example, other example medical devices may require that the RX port 112 be positioned a substantial distance (e.g., greater than about 50 millimeters) away from the functional portion of the medical device.

The location of the RX port 112 along the shaft 102 may help to determine the size or cross-sectional dimension of the RX port 112, which may vary. The RX port 112 may have virtually any cross-sectional dimension that permits a guidewire 114 to be effectively passed through the RX port 112 and into the medical device 100. Moreover, the cross-sectional dimension of the RX port 112 may also be capable of allowing the guidewire exchange device 200 (to be discussed below) to engage the RX port 112 properly. In one embodiment the guidewire exchange device 200 engages the RX port 112 by having a portion of the guidewire exchange device 200 at least partially enter the RX port 112. In other embodiments, the guidewire exchange device 200 engages the RX port 112 by surrounding the circumference of the RX port 112. Thus, the cross-sectional dimension of the RX port 112 may vary depending, at least in part, on the engagement configuration of the guidewire exchange device 200. An example RX port 112 cross-sectional dimension includes, but is not limited to, about one millimeter. The cross-sectional dimension of the RX port 112 may be greater or smaller than one millimeter depending on the type and configuration of the medical device 100.

Notwithstanding the cross-sectional dimension of the RX port 112, the angle at which the RX port 112 is oriented with respect to the shaft 102 of the medical device 100 is another way in which the RX port 112 may vary. For example, and as shown in FIG. 1C, the RX port 112 is substantially parallel with the shaft 102 of the medical device 100, i.e., the cross-sectional plane of the RX port 112 is oriented parallel to the shaft 102. In other example embodiments, the RX port 112 may be configured such that the RX port 112 is at an angle with respect to the shaft 102. For example, the RX port 112 may be configured such that the cross-section plane is oriented at an angle with respect to the shaft 102.

In instances where the RX port 112 has an angled orientation, the RX port may create a slight protrusion on the portion of the RX port towards the distal end of the shaft and/or the angled RX port 112 may create an indentation on the portion of the RX port 112 towards the proximal end of the shaft. The protrusion and/or indentation may be further configured to assist in engaging the guidewire exchange device 200. For example, the protrusion may be configured as a hook that interfaces with the guidewire exchange device 200 in a way that directs or assists to direct the guidewire exchange device 200 to operatively interface with the RX port 112. Furthermore, the indentation that may be formed on the RX port 112 towards the proximal end 104 of the shaft 102 may be configured as a channel to lead the guidewire exchange device 200 to operatively interface with the RX port 112.

The medical device 100, as shown in FIG. 1C, is only one example of a medical device 100 that may be used with the present invention. The present invention may be used with any medical device that includes an RX port or may be configured to include an RX port. For example, medical devices that may not currently include an RX port may be configured in the future with an RX port such that the medical device may be used with the present invention.

In addition to the various types and configurations of the medical device 100, the guidewire 114 that is used in conjunction with the medical device 100 may vary from one embodiment to the next. For example, the guidewire 114 may be made from various materials. Particularly, guidewire 114 may be made from metallic materials such as stainless steel or stainless steel alloys that include various weight ratios of one or more of the following materials: carbon, manganese, silicon, molybdenum, copper, chromium, nickel and or any other material that is known in the art to make guidewires. The guidewire 114 may be made from virtually any material that allows the guidewire to have sufficient column strength to be pushed through a patient's vascular system or other body lumens without kinking, while at the same time having sufficient flexibility to avoid damaging the blood vessel or other body lumen through which they are advanced.

The material of the guidewire 114 may partially determine the cross-sectional dimension of the guidewire 114. Generally speaking, the cross-sectional dimension of the guidewire 114 may be less than the cross-sectional dimension of the RX port 112 such that the guidewire 114 may be passed through the RX port 112 and extend through the medical device 100. Moreover, the guidewire 114 cross-sectional dimension may be sized to permit the guidewire 114 to be inserted and extend through the guidewire exchange device 200. Examples of a cross-sectional dimension of the guidewire 114 may range from about 0.014 inches to about 0.025 inches. Of course, the cross-sectional dimension of the guidewire 114 may be larger or smaller depending on the medical device 100 configuration and/or the medical procedure.

Although FIG. 1C illustrates the cross-sectional dimension of the guidewire 114 as being substantially constant throughout the guidewire 114, the guidewire 114 cross-sectional dimension may vary throughout the guidewire 114. For example, a distal end portion of the guidewire 114 may have a smaller cross-sectional dimension than other portions of the guidewire 114. In this way, the smaller cross-sectional distal end portion may be configured to more easily be inserted into the RX port 112 of the medical device 100.

The above discussion of the guidewire 114 also is applicable to a second guidewire that may be inserted into the medical device 100 by using the guidewire exchange device 200.

FIG. 2A shows one example of a guidewire exchange device 200. Structurally, the guidewire exchange device 200 includes a hollow elongate body 202 that creates a passage 232 that extends from a proximal end 204 to a distal end 206. Coupled to the distal end 206 of the elongate body 202 is a tip portion 208. The tip portion 208 may include a tapered portion 210 and be configured to cooperate with the passage 232 in the elongate body 202. The guidewire exchange device 200 may also include a proximal grip 212 positioned between the proximal end 204 and the distal end 206 of the elongate body 202. A grip extension 222 may additionally be positioned at the distal end 206 of the guidewire exchange device 200 and at least partially cover the tip portion 208. A retainer 224 may be used to secure the grip extension 222 to the elongate body 202 of the guidewire exchange device 200.

As a brief operational overview, the guidewire exchange device 200 engages and interfaces with the medical device 100 in a way that permits the guidewire 114 associated with the medical device 100 to be removed, and for a second guidewire to be inserted into the medical device 100. More specifically in one embodiment, the tip portion 208 of the guidewire exchange device 200 interfaces with the RX port 112 of the medical device 100 while the proximal grip 212 and/or the grip extension 222 engage the shaft 102 of the medical device 100. Thus, the guidewire exchange device 200 is secured in place adjacent to the medical device 100 such that the guidewire 114 may be safely removed and a new guidewire optionally inserted without loosing or substantially changing the position of the medical device 100 within the anatomy of a patient.

The structure and configuration of the guidewire exchange device 200 may vary from one embodiment to the next. For example, one aspect of the guidewire exchange device 200 that may vary is the elongate body 202. In one embodiment, as illustrated in FIGS. 2A and 2B, the elongate body 202 is an extruded tubular member with a substantially circular cross-section. In other embodiments, the cross-section of the elongate body 202 may have alternative configurations. For example, the cross-section configuration of the elongate body 202 may be oval, square or any other configuration.

In addition to the cross-section configuration of the elongate body 202, the cross-sectional dimension of the elongate body 202 may vary from one embodiment to the next or within the same embodiment. For example, in one embodiment the cross-sectional dimension of the elongate body 202 may be about one millimeter. In other embodiments, however, the cross-sectional dimension may be larger or smaller.

One characteristic of the elongate body 202 that may determine the cross-sectional dimension is the number of passages 232 that may extend through the elongate body 202. As shown in FIGS. 2A and 2B, the elongate body 202 includes a single passage 232. In another example embodiment, the elongate body 202 may be configured with more than one passage 232. For example, the elongate body 202 may include two, three or more passages such that each separate passage may be used to facilitate a separate guidewire and/or other medical device. For instance, a first passage may be used to remove a first guidewire from the medical device 100, while a second passage may be used to stage and introduce a second guidewire into the medical device 100.

In conjunction with the geometric configuration of the elongate body 202, the passage(s) 232 that extend through the elongate body 202 may vary from one embodiment to the next. For example, and as illustrated in FIG. 2B, the passage 232 has a generally circular cross-sectional configuration. In other embodiments, the passage 232 may have various cross-sectional configurations such as square, oval, rectangular or any other configuration or combination of configurations that would allow a guidewire to pass through the passage 232.

Another way in which the passage 232 may vary is the size or cross-sectional dimension of the passage 232. In one embodiment, the passage 232 has a cross-sectional dimension of about one-half millimeter. However, the cross-sectional dimension of the passage 232 may be larger or smaller depending on the specific embodiment (e.g., the number of passages within the elongate body 202) and/or the cross-section dimension of the guidewire 114, as discussed above.

In addition to various geometric configurations, the elongate body 202 material may vary from one embodiment to the next. In one embodiment, the elongate body 202 is made from extruded thermoplastic. Other example materials that may be used to make the elongate body 202 include, but are not limited to, various types of metals, plastics, composites and/or any material or combination of materials. Some example materials may be flexible such that as the guidewire exchange device 200 is moved through a tortuous path inside a body lumen, the elongate body 202 may flex and bend around the curves and bends in the body lumen.

As mentioned, the elongate body 202 of the guidewire exchange device 200 may have a tip portion 208 that is attached or coupled to the distal end 206 of the elongate body 202. The tip portion 208 is another aspect of the guidewire exchange device 200 that may vary from one embodiment to the next. For example, the way in which the tip portion 208 is attached or coupled to the elongate body 202 may vary. As illustrated in FIG. 2A, the tip portion 208 may be coupled to or otherwise attached to the elongate body 202 by way of a retainer 224. In particular, the retainer 224 may exert a radial compressive force on both the elongate body 202 and the tip portion 208 sufficient to secure the tip portion 208 in a position adjacent to the elongate body 202. In one embodiment, the elongate body 202 or the tip portion 208 may include a sleeve that is configured to overlap the joint between the elongate body 202 and the tip portion 208. In this embodiment, the retainer 224 may be positioned to exert a force upon the sleeve so as to secure the elongate body 202 and the tip portion 208 together.

The retainer 224 may have various configurations, for example, retainer 224 may be a weld ring that is used to secure the tip portion 208 to the elongate body 202. In one example embodiment, the retainer 224 may be a PET shrink tube. In other embodiments, the retainer 224 may be an adhesive tape or other material that creates an adhesive bond between the tip portion 208 and the elongate body 202. In yet other embodiments, the tip portion 208 may be attached or coupled to the elongate body 202 by a direct bonding agent (e.g., glue), or alternatively, the tip portion may be formed out of the same piece of material as the elongate body 202, thus, negating the need for a retainer 224.

The manner used to attach or couple the tip portion 208 to the elongate body 202 may depend on the cross-sectional dimension of the tip portion 208, which may vary from one embodiment to the next. For example, the cross-sectional dimension of the tip portion 208 may vary with respect to the cross-sectional dimension of the elongate body 202. As illustrated in FIG. 2A, the tip portion 208 has substantially the same cross-sectional dimension as the elongate body 202. However, in other embodiments the tip portion 208 may have a larger or smaller cross-sectional dimension when compared to the elongate body 202. In particular, it may be advantageous to have a tip portion 208 with a smaller cross-sectional diameter than the elongate body 202 such that the tip portion 208 may more easily interface with the RX port 112 of the medical device 100. Some example cross-sectional dimensions of the tip portion 208 may range from about 0.75 millimeter to 1.25 millimeter, but may be larger or smaller depending on the configuration and cross-sectional dimension of the RX port 112.

In order to further configure the tip portion 208 to more easily interface with the RX port 112 of the medical device 100, the tip portion may include a tapered portion 210 as shown in FIGS. 2A and 2C. The tapered portion 210 configuration may vary from one embodiment to the next. For example, and as shown in FIG. 2A, the tapered portion 210 has a cross-sectional dimension that varies from a larger cross-sectional dimension to a smaller cross-sectional dimension moving from the proximal end towards the distal end of the tip portion 208.

The rate at which the cross-sectional dimension changes may vary from one embodiment of the tapered portion 210 to the next. As shown in FIG. 2A, the rate of change in the cross-sectional dimension is small such that the tapered portion 210 slowly changes cross-sectional dimension to reach a final tip portion dimension located at the distal end of the tip portion 208. In one embodiment, the final tip portion diameter is about 0.38 millimeter, but may be larger or smaller depending on the specific embodiment. In other embodiments, the rate at which the cross-sectional dimension of the tapered portion 210 varies may be substantially larger such that the angle of the tapered portion 210 is more abrupt, thus, causing the tapered portion 210 to quickly change from one cross dimensional size to a smaller cross dimensional size. In one embodiment, the tapered portion may represent a stepped transition directly from a larger cross-sectional dimension to a smaller cross-sectional dimension.

Another way in which the tip portion 208 may vary is the length of the tip portion. An example tip portion length range from about five millimeters to about fifteen millimeters. However, the length of the tip portion 208 may be larger or smaller depending on the configuration of the tip portion 208 and the guidewire exchange device 200. In one example, the tip portion 208 may be configured such as to extend through the RX port 112 and partially extend into the RX port 112 of the medical device 100.

Another way in which the tip portion 208 may vary is the orientation that the tip portion 208 takes with respect to the elongate body 202. For example, and as illustrated in FIG. 2A, the tip portion 208 may be substantially parallel with the elongate body 202. However, in other embodiments, and as illustrated in FIG. 4, the tip portion 208 may be oriented at an angle with respect to the elongate body 202. The angled orientation of the tip portion 208 with respect to the elongate body 202 may provide for easier interfacing between the tip portion 208 and the RX port 112 of the medical device 100.

Example angles of the tapered portion 210 with respect to elongate body 202 may range from about five degrees to about forty-five degrees. However, the angle of orientation of the tapered portion 210 with respect to the elongate body 202 may be larger or smaller depending on the orientation of the RX port 112 and/or other design configurations of the guidewire exchange device 200 or medical device 100. In one example embodiment, the tip portion 208 has an orientation such that the tip portion 208 is angled about fifteen degrees from the elongate body 202.

Instead of being designed with a permanent angle orientation, the tip portion 208 may be made from a material that is able to flex or bend to create an angle. One example of a tip portion 208 material may include, but is not limited to, a malleable durometer thermoplastic material that provides a flexible soft tip such that the tip may be capable of flexing or bending to engage the RX port 112 located on the medical device 100. Other example tip portion 208 materials include synthetic rubber, natural rubber, various other plastics and/or composites that may be flexible such as to facilitate engagement between the tip portion 208 and the RX port 112. Additionally, the tip portion 208 material may be loaded with tungsten, or another radiopaque material, such that the user may visualise the location of the tip portion while the guidewire exchange device [200] is within the body of the patient. Loading a radiopaque material would provide tip portion 208 visibility while within the patient, and at the same time not increase the profile size of the tip portion 208 because no extra material layer would need to be added to provide a radiopaque layer.

In one embodiment of the invention, the grip extension 222 may be configured to at least partially cover the tip portion 208 and provide a downward force on the tip portion 208 such that the tip portion 208 may bend downward towards the RX port 112, as illustrated in FIG. 4. The grip extension 222 may be configured to constantly provide the tip portion with the downward force, or alternatively, the grip extension 222 may only provide the downward force to the tip portion 208 when the grip extension 222 is engaged with the shaft 102 of the medical device 100. In another embodiment, the guidewire 114 may provide enough force on the tip portion 208 such as to flex or bend the tip portion 208 into the RX port 112.

Figure 6:
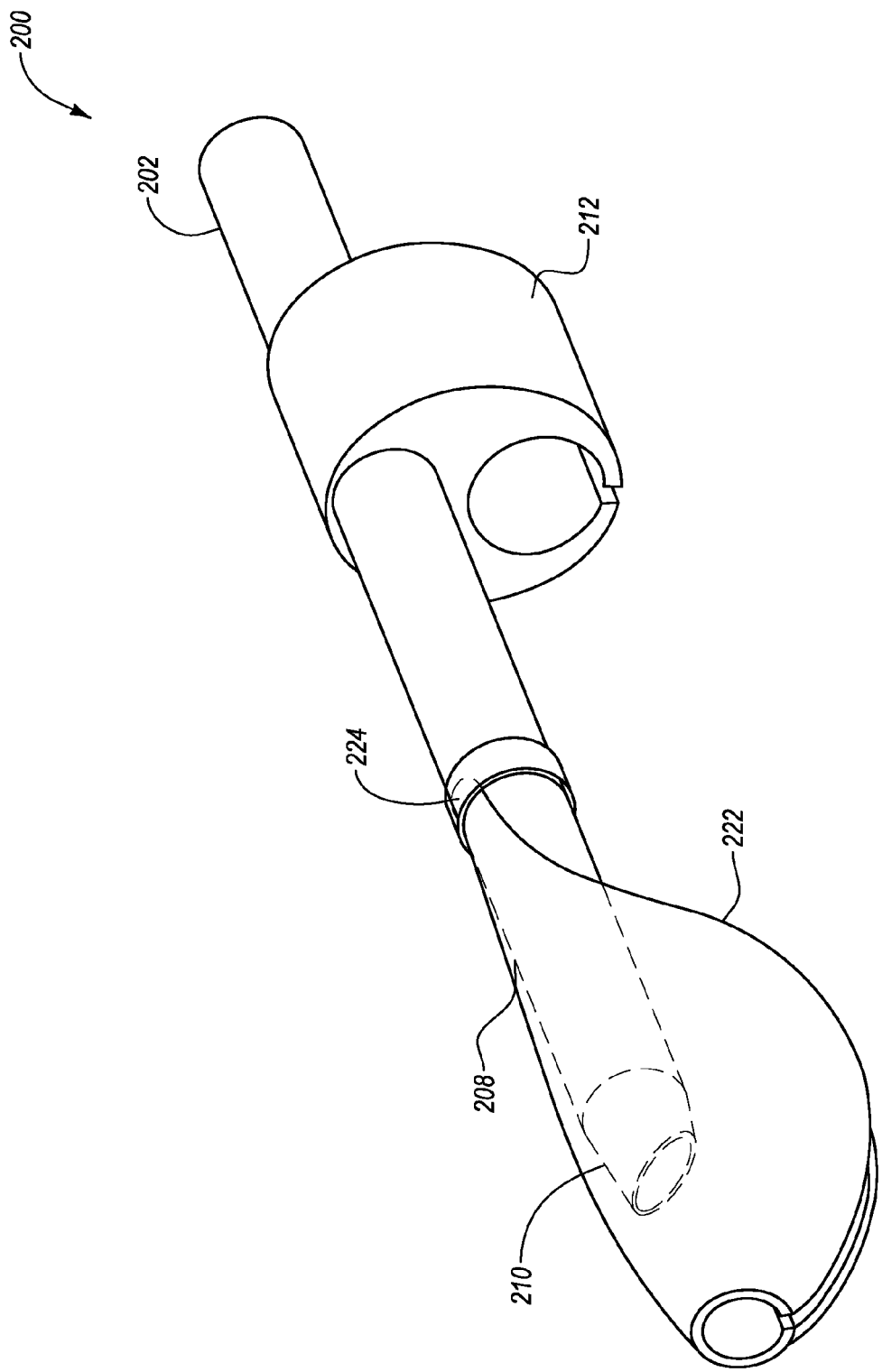
FIG. 6 is an illustration of another example embodiment of a guidewire exchange device.

Another geometric configuration of the tip portion 208 that may vary is the geometric configuration of the aperture located at the distal end of the tip portion 208. For example, and as illustrated in FIG. 2A, the aperture may have a substantially circular cross-section on the distal end of the tip portion 208, wherein the aperture is aligned along an axis of the tip portion 208. In another example embodiment, illustrated in FIG. 6, the aperture on the tip portion 208 may be configured and oriented such that the aperture may be at an angle with respect to the axis of the tip portion 208, thus, increasing the cross-sectional area of the aperture. In this embodiment, the placement of the aperture may further facilitate guidewire exchange by ensuring contact of the tip portion 208 within the RX port 112 of the medical device 100. In addition, this configuration may further provide greater surface area contact between the tip portion 208 and the RX port 112. Further still, the embodiment shown in FIG. 6 may provide better compatibility across various RX port designs of existing catheters.

Continuing with FIG. 2A, the guidewire exchange device 200 may further include a proximal grip 212. FIG. 2B shows a cross-sectional view of the proximal grip 212 at the plane marked 2B in FIG. 2A. As shown in FIG. 2B, the proximal grip 212 includes a first proximal grip member 214 and a second proximal grip member 216. The first and second proximal grip members 214 and 216 are separated by a proximal grip slit 218. The first proximal grip member 214 and the second proximal grip member 216 are configured and oriented such that they are able to flex and/or stretch about the proximal grip slit 218 upon being pressed onto the shaft 102 of the medical device 100 such that the shaft 102 of the medical device may be engaged within a medical device pocket 220 within the proximal grip 212. For example, the medical device pocket 220 may have a smaller cross-sectional dimension relative to a cross-sectional dimension of the medical device 100.

The proximal grip 212 may vary from one embodiment to the next, for example, the proximal grip 212 material may vary. For instance, the proximal grip 212 may be made from a malleable durometer thermoplastic material such that the material is able to flex and/or stretch slightly to accept the shaft 102 in the proximal grip slit 218 between the first and second proximal grip members 214 and 216. The proximal grip 212 material may also have a sufficient potential energy property such that once the shaft 102 of the medical device 100 has been encompassed and circumscribed by the first and second proximal grip members 214 and 216, the material is inclined or biased to close around the circumference of the shaft 102 of the medical device 100. Moreover, the material may be configured to provide a modest compressive force to the shaft 102 of the medical device 100 to prevent the loss of position of the medical device 100 during the exchange of the guidewire 114. For example, the first and second proximal grip members 214 and 216 are additionally sized such that the medical device pocket 220, in a resting state, has a distance between the first and second proximal grip members 214 and 216 that is less than the diameter of the shaft 102 of the medical device 100.

In addition to configuring the proximal grip 212 with various material properties to assist in securing the shaft 102 of the medical device 100 within the medical device pocket 220, the first and second proximal grip members 214 and 216 may include various surface features that help secure the shaft 102 of the medical device 100. For example, the inner surfaces of the first and second proximal grip member 214 and 216 that form the medical device pocket 220 may include protrusions or a tread pattern that is configured to not allow the shaft 102 of the medical device 100 to rotate while encompassed within the medical device pocket 220 of the proximal grip 212. Moreover, the edges of the first and second proximal grip members 214 and 216 may be angled such that the shaft 102 of the medical device 100 may more easily expand the proximal grip slit 218 while being pressed into the medical device pocket 220.

The length of the proximal grip 212 may also be configured to assist in securing the shaft 102 of the medical device 100 during the exchange of the guidewire 114. Example lengths of the proximal grip 212 may range between about five millimeters and about fifteen millimeters. Of course, the length of the proximal grip 212 may be longer or shorter. Generally, the longer the proximal grip, the more secure the proximal grip 212 engages the shaft 102 of the medical device 100.

Similar to the length of the proximal grip 212, the distance to which the proximal grip 212 extends away from the guidewire exchange device 200 may vary from one embodiment to the next. For example, the proximal grip 212, as shown in FIG. 2A, is configured such that it extends only a short distance away from the guidewire exchange device 200 such that the medical device 100, when gripped by the proximal grip 212, is held close to the guidewire exchange device 200. In another example embodiment, the distance between the guidewire exchange device 200 and the medical device 100 gripped within the proximal grip 212 may be longer. For example, the proximal grip 212 may be designed such that it extends away from the guidewire exchange device 200 so as to engage and secure the medical device 100 at a distance in the range of about 0.5 millimeters to about five millimeters away from the elongate body 202 of the guidewire exchange device 200. Distances may be longer or shorter depending on the overall configuration and function of the guidewire exchange device 200 and/or the configuration and function of the medical device 100.

Similar to the proximal grip 212, the guidewire exchange device 200 may include the grip extension 222, as illustrated in FIGS. 2A and 2C, that may be configured to engage the medical device 100 about the portion of the medical device 100 that includes the RX port 112. As illustrated in FIG. 2C, the grip extension 222 may include a first grip extension member 226 and a second grip extension member 228. The first and second grip extension members 226 and 228 may be separated by a grip extension slit 230, which leads to a RX port pocket 236. The grip extension 222 is configured to engage and secure the medical device 100 about the RX port 112 such that the guidewire exchange device 200 may remove the guidewire 114 from the medical device 100, and if needed, introduce a new guidewire into the medical device. The grip extension 222 may be configured to cause the tip portion 208 to deflect towards the RX port 112 of the medical device 100. The RX port pocket 236 may be formed by the first grip extension member 226 and the second grip extension member 228. The RX port pocket 236 may have a center axis that is offset from a center axis of the elongate body 202.

As illustrated in FIG. 2A, the grip extension 222 is configured to at least partially cover, if not totally cover, the entire tip portion 208 and tapered portion 210 of the guidewire exchange device 200. Moreover, and as illustrated in FIG. 2A, the grip extension 222 may be configured with a length that extends past the tip portion 208 and/or tapered portion 210 of the guidewire exchange device 200. The extent to which the grip extension 222 extends past the tip portion 208 and/or tapered portion 210 may vary from one embodiment to the next. In one example, the grip extension 222 extends past the tapered portion 210 of the tip portion 208 in a range of about five millimeters to about fifteen millimeters. In another embodiment, the grip extension 222 may not extend past the tapered portion 210 at all, or alternatively, the tapered portion 210 may extend past the grip extension 222.

The extent to which the grip extension 222 extends past the tip portion 208 is not the only geometric configuration of the grip extension 222 that may vary. For example, the cross-sectional dimension of the grip extension 222 may also vary from one embodiment to the next. In one example embodiment, the cross-sectional dimension ranges from about one millimeter to about two millimeters. Depending on the medical procedure or other factors, however, the cross-sectional dimension of the grip extension 222 may be larger or smaller.

The overall geometric configuration of the grip extension 222 may also vary. As illustrated in FIGS. 2A and 2C, the grip extension 222 has a semi-circular side cross-sectional configuration (FIG. 2A) and an oval end cross-sectional configuration (FIG. 2C). The side cross-sectional configuration may take almost any configuration, such as square, rectangular or trapezoidal as long as the configuration provides for a means to engage the medical device 100 proximate to the RX port 112. Similarly, the end cross-sectional configuration may take almost any configuration, such as square, triangular, rectangular and octagonal or any other configuration or combination of configurations.

The overall geometric configuration may affect the operational properties of the grip extension 222. For example, and as shown in FIG. 2A, the grip extension 222 may be configured to allow the tip portion 208 to extend generally parallel to the elongate body 202 of the guidewire exchange device 200. In another example, illustrated in FIG. 4, the grip extension 222 may be configured to apply a downward pressure on the tip portion 208 to assist the tip portion 208 in interfacing with the RX port 112 and to reduce the likelihood of the tip portion 208 lifting out of the RX port 112 when removing the guidewire 114. In one embodiment, the grip extension 222 is configured to transform from the configuration illustrated in FIG. 2A to the configuration illustrated in FIG. 4 as the first and second grip extension members 226 and 228 open to engage the medical device 100. Thus, as the first and second grip extension members 226 and 228 open to engage the medical device 100, the grip extension 222 may apply a downward pressure on the tip portion 208 directing the tip portion 208 downward towards the RX port 112.

As with the proximal grip 212, the grip extension may have various characteristics that assist to engage and secure the medical device 100. For example, the ends of the first and second grip extension members 226 and 228 may be angled such as to easily engage the medical device 100. Moreover, the inner walls of the first and second grip extension members 226 and 228 may include protrusions or thread designed to engage the medical device 100 such as to prevent the medical device 100 from rotating axially within the RX port pocket 236 of the grip extension 222.

In addition to the various configurations and characteristics of the grip extension 222, the way in which the grip extension is attached or coupled to the guidewire exchange device 200 may vary from one embodiment to the next. For example, and as illustrated in FIG. 2A, the grip extension 222 may be coupled onto the distal end 206 of the elongate body 202 of the guidewire exchange device 200 by way of a retainer 224. The retainer 224 may be the same retainer that is used to secure the tip portion 208 to the elongate body 202. Alternatively, the retainer 224 may be a separate retainer.

Another way in which the grip extension 222 may vary is the material used to make the grip extension. For example, the grip extension 222 may be made from any flexible material such as plastic, natural or synthetic rubber, thermoplastic or any other composite that is able to provide some flexibility as well as provide a clamping force between the first grip extension member 226 and the second grip extension member 228. In addition, the grip extension 222 may be configured to include the same material properties as the proximal grip 212 discussed above.

Depending on the material used to make the grip extension 222, the first and second grip extension members 226 and 228 may take various configurations. For example, FIGS. 5A and 5B show two example embodiments of a cross-sectional elevation view of the grip extension 222. FIG. 5A illustrates one embodiment where the first grip extension member 226 and the second grip extension member 228 are configured such that the tips of each of the first and second grip extension members 226 and 228 align and are separated by the grip extension slit 230. In this configuration the grip extension 222 may be placed on the shaft 102 of the medical device 100 and pressed downward such that the first grip extension member 226 and second grip extension member 228 slightly move radially outward so that the shaft 102 of the medical device 100 may be pressed into the expanding grip extension slit 230. Once pressed through the grip extension slit 230 the shaft 102 may be positioned between the first grip extension member 226 and the second grip extension member 228 in the RX port pocket 236. For example, the RX port pocket 236 may have a smaller cross-sectional dimension relative to a cross-sectional dimension of the medical device 100.

FIG. 5B illustrates another example embodiment of the grip extension 222. In FIG. 5B the first grip extension member 226 and the second grip extension member 228 are configured in a folded wing configuration. In the folded wing configuration, the first grip extension member 226 is made to be folded into the second grip extension member 228 such that the inside surface of the second grip extension member 228 interacts with the outside surface of the first grip extension member 226, as illustrated in FIG. 5B. The folded wing configuration of the grip extension 222 in FIG. 5B is configured such that the shaft 102 of the medical device 100 may be placed at the intersection of the first grip extension member 226 and the second grip extension member 228. The grip extension 222 may then be rolled or twisted radially about the axis of the guidewire exchange device 200 such that the shaft 102 of the medical device 100 is able to enter between the first grip extension member 226 and the second grip extension member 228 until the shaft 102 is securely held by both the first grip extension member 226 and the second grip extension member 228 in the RX port pocket 236. The RX port pocket 236 may have an open configuration and a closed configuration. For example, in the open configuration, the first grip extension member 226 and the second grip extension member 228 may be separated by a distance equal to or greater than a cross-sectional dimension of the medical device 100. In the closed configuration, the first grip extension member 226 and the second grip extension member 228 may be separated by a distance less than the cross-sectional dimension of the medical device 100.

In another example embodiment, a separator bar may be placed between the first and second grip extension members 226 and 228 such that the separator bar expands the grip extension slit 230. For instance, the separator bar may be placed within the RX port pocket 236 of the grip extension 222. The separator bar may be configured to hold open the grip extension slit 230 until the medical device 100 comes into contact with the separator bar. When the medical device 100 contacts the separator bar, the separator bar may be configured to collapse or give way such that the first and second grip extension members 226 and 228 may engage the medical device 100. Other similar or equivalent configurations of the grip extension 222 may be used.

During use, the guidewire exchange device 200 may have various operational embodiments to exchange a guidewire from the medical device 100. For example, FIG. 3A through 3C shows one operational embodiment where the guidewire exchange device 200 has engaged the medical device 100. As illustrated in FIG. 3A, the guidewire 114 has been back-loaded into the guidewire exchange device 200 such that the guidewire extends through the tip portion 208 and the elongate body 202. Moreover, the proximal grip 212 has engaged the shaft 102 of the medical device and the grip extension 222 has also engaged the shaft 102 of the medical device proximal to the RX port 112. In particular, FIG. 3B illustrates that the shaft 102 of the medical device 100 is secured between the first and second proximal grip members 214 and 216, and FIG. 3C illustrates the shaft 102 of the medical device 100 is secured between the first and second grip extension members 226 and 228.

In the embodiment illustrated in FIG. 3A, the guidewire exchange device 200 may be configured such that the guidewire exchange device 200 is engaged to the medical device 100 outside of the patient's body and then subsequently moved along the medical device 100 shaft 102 until reaching the RX port 112. In other example embodiments, the guidewire exchange device 200 may be inserted within the anatomy of the patient and then subsequently engage the medical device 100. In one embodiment, the guidewire exchange device 200 may not engage the medical device 100 until the tip portion 108 or tapered portion 110 is aligned to interface with the RX port 112 on the medical device 100.

To assist in aligning the tip portion 208 of the guidewire exchange device 200 with the RX port 112 on the medical device 100, the tip portion 208 and the RX port 112 may be marked with a radiopaque material such that a user may track the position of the tip portion 208 with respect to the RX port 112. In other embodiments, measurement markings may be located on the portion of both the medical device 100 and the guidewire exchange device 200 that is located outside of the patient such that a user may monitor the distance to which each of the devices is inserted into the anatomy of the patient. For example, the measurement markings may be a printed or hot foil marker that aligns with, for example, brachial and/or femoral markers that may be included on the shaft 102 of the medical device 100. In one embodiment, a single low profile print or hot foil marker may be placed to indicate a specific distance from the marker to the RX port 112 and/or tip portion 208.

FIG. 4 illustrates an example embodiment of the guidewire exchange device 200 where the tapered portion 210 has interfaced with the RX port 112 of the medical device 100. The tapered portion 210 in this embodiment may be a tapered portion 210 that includes an angle such that the tapered portion 210 naturally angles into the RX port 112 as shown. Alternatively, the tapered portion 210 may not necessarily include an angle; rather, the tapered portion 210 may be made of a flexible material such that the tapered portion may follow the guidewire 114 and bend in order to interface with the RX port 112.

In any event, once the tapered portion 210, or alternatively the tip portion 208, interfaces with the RX port 112, the guidewire 114 may be removed from the medical device 100 and a replacement guidewire may be installed within the medical device 100. Once the new guidewire is installed (if needed) then the guidewire exchange device 200 may be removed from the patient or from the medical device 100. In one example, the guidewire exchange device 200 disengages from the medical device 100 while within the anatomy of the patient and is then removed from the patient. In another embodiment, the guidewire exchange device is allowed to slide along the shaft 102 of the medical device 100 until outside of the patient's anatomy. After the removal of the guide wire exchange device 200, the user may continue with normal use of the medical device 100 as necessary.

The tip of the guidewire exchange device 200 is capable of being juxtaposed and/or interlocked with the lumen of the port of the medical device with which the guidewire exchange device 200 is being used. The tip or tapered portion is often shaped to ensure an intimate connection when conjoined with the RX port 112 of the medical device 100. As previously mentioned, a tip that is angled may be able to provide a better interface with the port, particularly when the tip or tapered portion is bent by the grip extension 222. In addition, an angled tip can also increase the surface area presented to the RX port 112, thus facilitating the exchange of guidewires. The tip may also be configured to be compatible with divergent types and configurations of RX ports 112.

Figure 7:
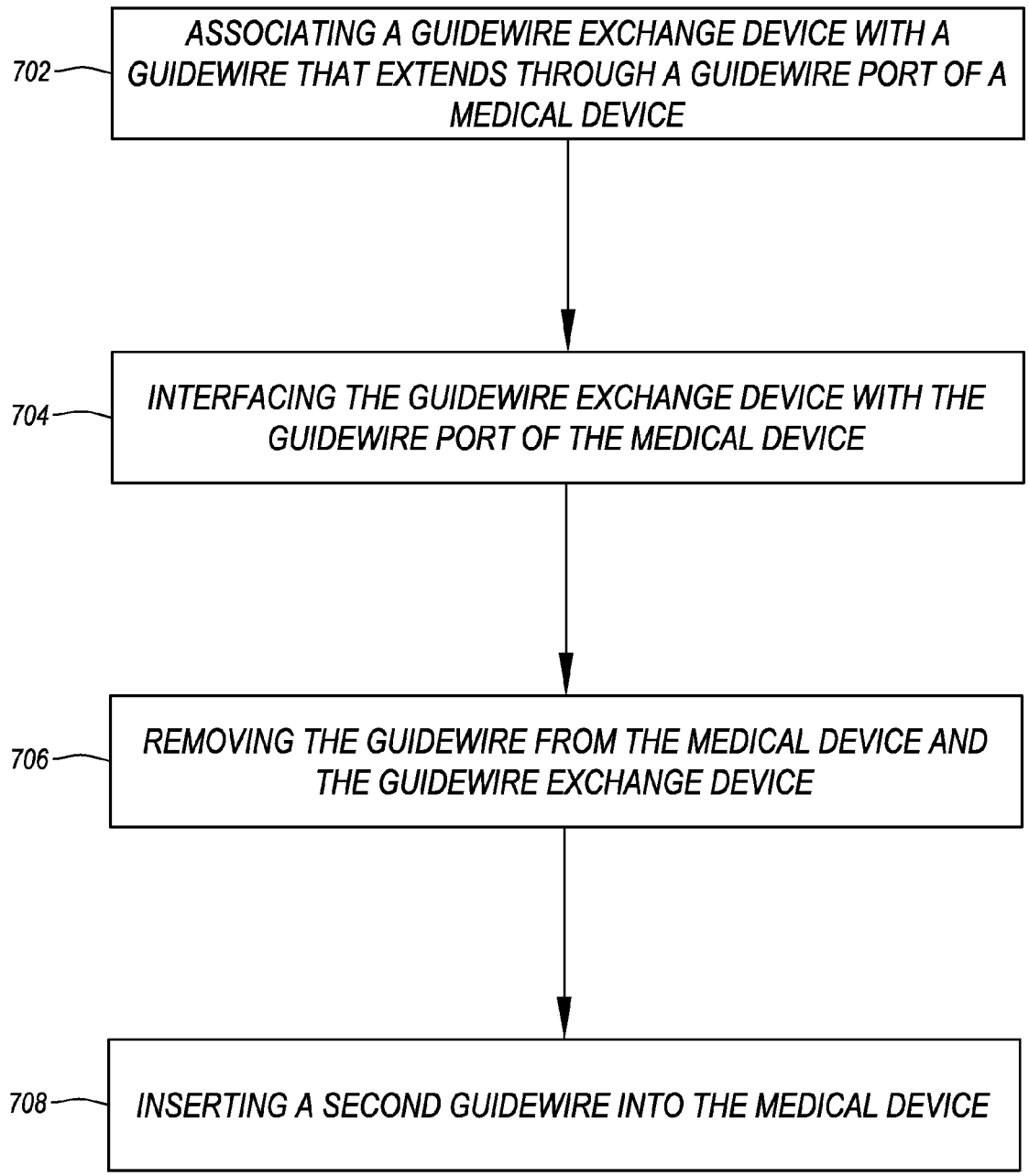
FIG. 7 is a flowchart illustrating a method of exchanging a guidewire.

Accordingly, the previous figures and the corresponding text provide a number of different components and systems that may be used to exchange a guidewire in a medical device while the medical device is within the anatomy of a patient. In addition to the foregoing, other example embodiments may also be described in terms of flowcharts comprising one or more acts in a method for accomplishing a particular result. For example, FIG. 7 illustrates a method of exchanging a guidewire in a medical device. The acts of FIG. 7 are discussed more fully below with respect to the disclosures of FIGS. 1A through 6.

For example, FIG. 7 shows that a method in accordance with an example implementation of the invention may include associating 702 a guidewire exchange device with a guidewire that extends through a guidewire port of a medical device. Associating a guidewire exchange device may involve disposing a guidewire exchange device over a guidewire, where the guidewire exchange device includes an elongate body having a proximal end, a distal end and a tip portion disposed adjacent to the distal end. For example, as shown in FIG. 3A, the guidewire 114 may be back-loaded through the guidewire device 200 such that the guidewire exchange device 200 may slide along the guidewire 114.

After the guidewire is associated with the guidewire exchange device, the guidewire exchange device interfaces 704 with the guidewire port of the medical device. Interfacing 704 the guidewire exchange device with the guidewire port may involve, for example, engaging a portion of the tip portion with a guidewire port of a medical device. For instance, the tapered portion 210 of the tip portion 208 may interface with the RX port 112 on the medical device 100, as illustrated in FIG. 4.

Removing 706 the guidewire from the medical device and the guidewire exchange device may then be performed. This may include removing the guidewire from the medical device and exchange device. For example, FIG. 4 illustrates that the guidewire 114 may be moved or pulled in the proximal direction such that the guidewire 114 is removed from the medical device 100 and the guidewire exchange device 200. As previously stated, this is often performed while the guidewire exchange device is associated with the medical device, for example, while the position of the guidewire exchange device is in a locked position or stop position relative to the medical device. Advantageously, the medical device does not need to be removed while the guidewire is exchanged for another guidewire.

The method of exchanging a guidewire may further include inserting 708 a second guidewire into the medical device. Specifically, this may include inserting a second guidewire into the exchange device and medical device. For example, as shown in FIG. 4, a second guidewire may be inserted in the proximal end of the elongate body 202 of the guidewire exchange device 200 and directed into the RX port 112 of the medical device 100 to a desired position. After the second guidewire is properly positioned, the guidewire exchange device can be disengaged from the medical device.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guidewire exchange device used to exchange a guidewire associated with a guidewire port on a medical device, the guidewire exchange device configured to interface with the guidewire port on the medical device, remove the guidewire associated with the medical device, and insert a replacement guidewire, the guidewire exchange device comprising:

an elongate body having a body proximal end, a body distal end, and a passage extending from the body proximal end toward the body distal end;

a tip portion having a tip proximal end and a tip distal end, the tip proximal end disposed adjacent to the body distal end of the elongate body, the tip portion configured to interface with the guidewire port of the medical device, and wherein an aperture located on the tip distal end cooperates with the passage in the elongate body; and a grip extension having a grip proximal end and a grip distal end, the grip extension at least partially covering the tip portion, and wherein the grip extension includes a first grip extension member and a second grip extension member that form a rapid exchange port pocket, the grip extension configured to cause the tip portion to deflect towards the guidewire port of the medical device.

2. The guidewire exchange device recited in claim 1, wherein the tip portion is tapered such that the cross-sectional dimension of the tip proximal end is larger than the cross-sectional dimension of the tip distal end.

3. The guidewire exchange device recited in claim 1, wherein the tip portion is oriented at an angle with respect to the elongate body.

4. The guidewire exchange device recited in claim 1, wherein the rapid exchange port pocket formed by the first grip extension member and the second grip extension member has a smaller cross-sectional dimension relative to a cross-sectional dimension of the medical device.

5. The guidewire exchange device recited in claim 4, wherein the rapid exchange port pocket has a center axis that is offset from a center axis of the elongate body.

6. The guidewire exchange device recited in claim 1, further comprising a proximal grip disposed on the elongate body of the guidewire exchange device, the proximal grip having a first proximal grip member and a second proximal grip member that form a medical device pocket.

7. The guidewire exchange device recited in claim 6, wherein the medical device pocket has a smaller cross-sectional dimension relative to a cross-sectional dimension of the medical device.

8. A guidewire exchange system for exchanging a first guidewire associated with a medical device with a second guidewire while the medical device is positioned within a body lumen, the system comprising:

a first guidewire and a second guidewire;

a medical device having a first configuration wherein the medical device is operatively associated with the first guidewire, and a second configuration wherein the medical device is operatively associated with the second guidewire and not the first guidewire, the medical device having a guidewire port; and a guidewire exchange device that is operatively associated with the medical device to change the medical device from the first configuration to the second configuration, the guidewire exchange device comprising:

an elongate body having a body proximal end, a body distal end, and a passage extending from the body proximal end toward the body distal end;

a tip portion having a tip proximal end and a tip distal end, the tip proximal end disposed adjacent to the body distal end of the elongate body, the tip portion configured to interface with the guidewire port of the medical device, and wherein an aperture located on the tip distal end cooperates with the passage in the elongate body; and a grip extension having a grip proximal end and a grip distal end, the grip extension at least partially covering the tip portion, and wherein the grip extension includes a first grip extension member and a second grip extension member that form a rapid exchange port pocket, the grip extension configured to cause the tip portion to deflect towards the guidewire port of the medical device.

9. The guidewire exchange system recited in claim 8, wherein the grip extension engages the medical device.

10. The guidewire exchange system recited in claim 9, the grip extension having an open configuration and a closed configuration, wherein the first grip extension member and the second grip extension member are separated by a distance equal to or greater than a cross-sectional dimension of the medical device in the open configuration, and wherein the first grip extension member and the second grip extension member are separated by a distance less than the cross-sectional dimension of the medical device.

11. A method for exchanging a guidewire in a medical device, comprising:

disposing a guidewire exchange device over a guidewire, the guidewire exchange device comprising:

an elongate body having a body proximal end, a body distal end, and a passage extending from the body proximal end toward the body distal end; and a tip portion having a tip proximal end and a tip distal end, the tip proximal end disposed adjacent to the body distal end of the elongate body, the tip portion configured to interface with a guidewire port of a medical device, and wherein an aperture located on the tip distal end cooperates with the passage in the elongate body; and a grip extension having a grip proximal end and a grip distal end, the grip extension at least partially covering the tip portion, and wherein the grip extension includes a first grip extension member and a second grip extension member that form a rapid exchange port pocket, the grip extension configured to cause the tip portion to deflect towards the guidewire port of the medical device;

engaging a portion of the tip portion with the guidewire port of the medical device; and removing the guidewire from the medical device.

12. The method according to claim 11, further including the step of inserting a second guidewire into the medical device through the tip portion.

13. The method according to claim 12, further including the step of disengaging the guidewire exchange device from the medical device.

14. The method according to claim 11, further including the step of securing the medical device to the guidewire exchange device.

15. The method according to claim 14, wherein securing the medical device to the guidewire exchange device further includes gripping the medical device with the grip extension.

16. The method according to claim 11, further including the step of aligning the tip portion with the guidewire port using radiopaque markers on the tip portion and the guidewire port.

* * * * *